US006989249B2

(12) United States Patent
Nalin et al.

(10) Patent No.: US 6,989,249 B2
(45) Date of Patent: Jan. 24, 2006

(54) METHOD FOR EXTRACTING DNA FROM ORGANISMS

(75) Inventors: Renaud Nalin, Caluire (FR); Patrick Robe, Francheville (FR); Van Tran Van, Villeurbanne (FR)

(73) Assignee: Libragen, Villeurbanne (FR)

( * ) Notice: Subject to any disclaimer, the term of this patent is extended or adjusted under 35 U.S.C. 154(b) by 526 days.

(21) Appl. No.: 10/282,190

(22) Filed: Oct. 28, 2002

(65) Prior Publication Data
US 2003/0049675 A1  Mar. 13, 2003

Related U.S. Application Data

(63) Continuation of application No. PCT/FR01/00992, filed on Apr. 3, 2001.

(51) Int. Cl.
*C12P 19/34*   (2006.01)
*C12N 1/08*    (2006.01)
*C07H 21/00*   (2006.01)
*C07H 1/08*    (2006.01)

(52) U.S. Cl. .................... 435/91.1; 435/270; 536/22.1; 536/127

(58) Field of Classification Search ............... 536/22.1, 536/23.1, 127; 435/89, 91.1, 270
See application file for complete search history.

(56) References Cited

U.S. PATENT DOCUMENTS 5,824,485 A   10/1998  Thompson et al. ............. 435/6
6,383,783 B1 *  5/2002  Haddad ...................... 435/91.1

FOREIGN PATENT DOCUMENTS

| EP | 0 388 053 A2 | 9/1990 |
| EP | 0 512 181 A1 | 11/1992 |
| EP | 0 939 118 A1 | 9/1999 |
| WO | WO 94/22904 | 10/1994 |
| WO | WO 97/12991 | 4/1997 |
| WO | WO 98/17685 | 4/1998 |
| WO | WO 99/08532 | 2/1999 |
| WO | WO 99/45154 | 9/1999 |

OTHER PUBLICATIONS

Amaral et al., "Atmospheric Methane Consumption by Forest Soils and Extracted Bacteria at Different pH Values," Applied and Environmental Microbiology, Jul. 1998, vol. 64, No. 7, pp. 2397-2402.
Romling et al., "The impact of two-dimensional pulsed-field gel electrophoresis techniques for the consistent and complete mapping of bacterial genomes: refined physical map of Pseudomonas aeruginosa PAO," Nucleic Acids Research, vol. 19, No. 12, 1991, pp. 3199-3206.
Suau et al., "Direct Analysis of Genes Encoding 16S rRNA from Complex Communities Reveals Many Novel Molecular Species Within the Human Gut," Applied and Environmental Microbiology, Nov. 1999, vol. 65, No. 11, pp. 4799-4807.
Rochelle et al., "A Simple Technique for Electroelution of DNA from Environmental Samples," BioTechniques, vol. 11, No. 6, (1991), pp. 724-728.
Griess et al., "Unlimited increase in the resolution of DNA ladders," Electrophoresis, vol. 21, (2000), pp. 859-864.
Amann et al., "Phylogenetic Identification and In Situ Detection of Individual Microbial Cells without Cultivation," Microbiological Reviews, vol. 59, No. 1, Mar. 1995, pp. 143-169.
Egly et al., "Electrophorese En Champs Alternes De L'Adn," Le Technoscope De Biofutur, No. 127, Oct. 1993, pp. 3-12.
Ranjard et al., "A single procedure to recover DNA from the surface or inside aggregates and in various size fractions of soil suitable for PCR-based assays of bacterial communities," Eur. J. Soil Biol., vol. 34, No. 2 (1998), pp. 89-97.
Seow et al., "A Study of Iterative Type II Polyketide Synthases, Using Bacterial Genes Cloned from Soil DNA: a Means To Access and Use Genes from Uncultured Microorganisms," J. of Bacteriology, vol. 179, No. 23, Dec. 1997, pp. 7360-7368.
Torsvik et al., "Total bacterial diversity in soil and sediment communities—a review," J. of Industrial Microbiology, vol. 17, (1996), pp. 170-178.
Frostegard et al., "Quantification of Bias Related to the Extraction of DNA Directly from Soils," Applied and Environmental Microbiology, vol. 65, No. 12, Dec. 1999, pp. 5409-5420.
Stein et al., "Characterization of Uncultivated Prokaryotes: Isolation and Analysis of a 40-Kilobase-Pair Genome Fragment from a Planktonic Marine Archaeon," J. of Bacteriology, vol. 178, No. 3, Feb. 1996, pp. 591-599.

* cited by examiner

*Primary Examiner*—David M. Naff
(74) *Attorney, Agent, or Firm*—Heslin Rothenberg Farley & Mesiti P.C.

(57) ABSTRACT

A method for the indirect extraction of DNA greater than 300 kb in size from non-cultivatable organisms contained in an environmental sample is disclosed. The method comprises isolating the organisms from the sample and embedding the isolated organisms in a block of agarose where the organisms are subsequently lysed and the DNA subjected to a first alternating field electrophoresis to extract DNA fragments which are large in size and separate them from the cell debris. The first electrophoretic migration is followed by an enzymatic restriction step and additional electrophoretic migrations. The invention also encompasses DNA obtained by the method.

12 Claims, 3 Drawing Sheets

METHOD FOR EXTRACTING DNA FROM ORGANISMS

CROSS REFERENCE TO RELATED APPLICATIONS

This application is a continuation of PCT Application PCT/FR01/00992 filed Apr. 3, 2001. PCT/FR01/00992 claimed the priority of French patent application 00.05274 filed Apr. 26, 2000, the entire disclosures of both are hereby incorporated by reference into the subject application.

FIELD OF THE INVENTION

The invention relates to a method for indirectly extracting DNA, in particular DNA fragments greater than 300 kB in size, of non-cultivatable organisms contained in an environmental sample. It also relates to the DNA, in particular that greater than 300 kB in size, which can be obtained by the method, and also to a DNA library consisting of the DNA fragments extracted by said method.

BACKGROUND OF THE INVENTION

In the context of the search for active molecules, and in particular for new antibiotics, amino acids, enzymes and vitamins, various methods are proposed, the principle of which is based on screening the metabolites produced by organisms originating from various environments. Thus, highly important products with antibiotic, anticancer or pesticidal activities have been isolated from microorganisms such as, for example, *Streptomyces, Nocardia* or *Actinoplanes*, etc.

Soil and sediments constitute major environments for searching for new active metabolites, not only by virtue of the very large amount of microorganisms which they contain, but also due to the considerable diversity of these microorganisms. It is known that the soil can contain from $10^9$ to $10^{11}$ bacteria per gram, of which a maximum of 1% are cultivatable on synthetic media (see R. I. AMANN, W. Ludwig, K H Schleifer (1995) "Phylogenetic identification and in situ detection of individual microbial cells without cultivate" Microbiological Review vol. 59 No. 11 143–169; W B Whitman, D C Coleman, W J Wiebe, 1998. Prokaryotes: The unseen majority, Proceeding National Academy of Science USA, Vol. 95: 6578–6583).

Moreover, the number of bacterial species per gram of soil is evaluated at 1,000 to 10,000. In fact, with DNA—DNA reassociation techniques, the results indicate that the genetic diversity of the microorganisms is certainly greater than 4 000 species per soil sample (Torsvik et al., 1990, Applied Environmental Microbiology, 56: 782–787). Still based on methods which do not involve culturing microorganisms in vitro, V. Torsvik, J. Goksoyr, F L. Daae, R. Sorheim, J. Michalsen and K. Salte, 1994, p. 39–48, in Beyond the Biomass, K. Ritz, J. Dighton and K. E. Giller (eds.), John Wiley and Sons, Chichester, indicate that the diversity of bacterial species may reach 13 000 species per 100 g of soil. Thus, estimating there to be $10^{10}$ bacterial cells per gram of soil, a bacterial species should be represented by an average of $10^6$ cells, even for the rarest species.

Moreover, bacteria have been detected in a large number of environments ranging from the stratosphere to the very depths of abysses, including the most extreme media in terms of physicochemical conditions. Thus, bacterial diversity is explained by a diversity of location of bacterial populations, first of all in terms of the macroenvironments which they have colonized, but also in terms of the microenvironments which characterize, for example, and in a non-limiting manner, the structuring of soils, as described by L. Ranjar, F. Poly, J. Combrisson, A. Richaume, S. Nazaret, 1998. A single procedure to recover DNA from the surface or inside aggregates and in various fractions of soil suitable for PCR-based assays of bacterial communities. European Journal of Soil Biology, 34(2), 89–97.

A large number of studies relating to bacterial diversity, based on the analysis of 16S rDNA ribosomal DNA genes, reveal the presence of many new phyla belonging to the domains of Archaebacteria, but also bacteria. The number of bacterial divisions identified has tripled in 10 years. Thus, the vast diversity of soil bacteria is still unknown. It is largely ignored in scientific research study and is not accessible and therefore not exploited industrially.

One of the objectives pursued is to gain access to this vast potential by extracting the DNA from the 99% of remaining non-cultivatable bacteria.

To do this, a first solution consists in improving culture media by increasing knowledge regarding the physiology of bacteria so as to make them cultivatable and therefore decrease the number of non-cultivatable bacteria. Such a technique has been used since the beginnings of microbiology and has produced very good results. In fact, close to 5,000 microorganisms have been described, all environments taken into account. Thus, more than 40,000 molecules have been characterized and close to half have biological activity. However, such a technique has the drawback of being relatively slow and tedious.

Another solution consists in directly extracting the DNA of non-cultivatable organisms from various environments by chemical and/or enzymatic lysis, as described, for example, in documents U.S. Pat. No. 5,824,485 or WO 97/12991, or else Antonia Suau et al., "Direct analysis of genes encoding 16S rRNA from complex communities reveals many novel molecular species within the human gut" APPLIED AND ENVIRONMENTAL MICROBIOLOGY, Vol. 65, No. 11, November 1999, pages 4799 and 4807, and P. S. ROCHELLE et al., "A simple technique for electroelution of DNA from environmental samples" BIOTECHNIQUES, Vol. 11, No. 6, 1991, pages 724, 726–728. The environments considered are either of the aquatic type, which requires concentration of the bacterial cells, as illustrated by the works of J. L. Stein, T. L. Marsh, K. Y. Wu, H. Shizuya and E. deLong, 1996—Characterization of uncultivated prokaryotes: isolation and analysis of a 40-kilobase-pair genome fragment from a planktonic marine archaeon, Journal of Bacteriology, 178: 591–599, or of the terrestrial type.

One of the main drawbacks of this direct extraction technique is that it leads to the extraction of only DNA which is small in size, of the order of a maximum of 1 to 23 kB. In fact, the physicochemical constraints which are imposed on the DNA during this type of experiment lead to its degradation. A. Frostegard, S. Courtois, V. Ramisse, S. Clerc, D. Bernillon, F. Le Gall, P. Jeannin, X. Nesme, P. Simonet, 1999. Quantification of bias related to the extraction of DNA directly from soils. APPLIED AND ENVIRONMENTAL MICROBIOLOGY, VOL. 65 (12): 5409–5420, clearly show that the improvement of DNA extraction yields, in particular by grinding or sonication techniques, leads to great degradation of the DNA recovered.

In addition, the extracted DNA comprises the extracellular DNA contained in the soil, but also the eukaryotic (fungi, plant cells, animal cells) and prokaryotic (bacteria) DNA and the other organisms present in the soil (protozoa, etc.). It results therefrom that the DNA libraries obtained are often highly contaminated with recombinant bacterial clones containing undesired DNA (eukaryotic DNA, degraded extracellular DNA). Moreover, the libraries thus constituted are characterized by DNA inserts which are small in size (less than 30 Kb). These libraries are not therefore suitable for applications such as the analysis of complete genomes or metagenomes, or the search for, study and exploitation of complete or virtually complete metabolic pathways.

Due to the dilution of the target DNAs by the non-target DNAs, it is consequently essential to selectively amplify the target DNA proportion by PCR so as to constitute appropriate DNA libraries, as described in the abovementioned Suau document. This approach has the main constraint of being able to access only genetic information similar to that already known, in fact excluding access to completely new and original DNA sequences. However, the use of defined PCR primers in very conserved regions has made it possible to isolate genes of interest belonging to nonisolated bacteria, as described, for example, by K. Seow, G. Meurer, M. Gerlitz, E. Wendt-Pienkowski, C. R. Hutchinson and J. Davies, 1997—A study of iterative type II Polyketide Synthases, using bacterial genes cloned from soil DNA: a means to access and use genes from uncultured microorganisms, Journal of Bacteriology, 179: 7360–7368.

Other selection methods have been developed. These methods consist in subjecting the bacterial community to a selection pressure making it possible to enrich given bacterial populations. It is thus hoped to have preferential access to the genetic information desired. Other selections based on the DNA composition (% GC) or its complexity have also been described, such as, for example, document WO 99/45154.

DETAILED DESCRIPTION

Figure 1:
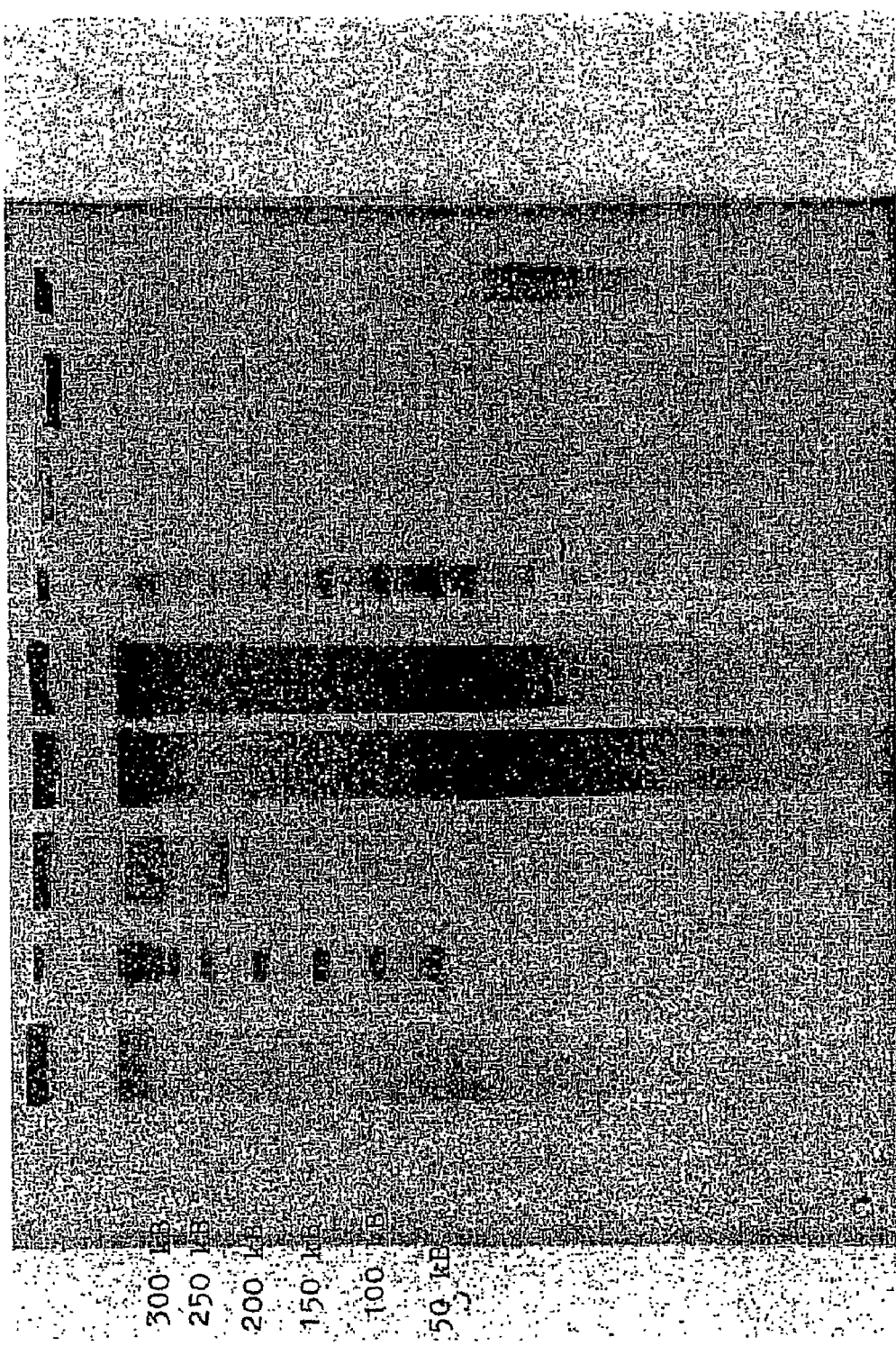
FIG. 1 represents the migration profile of the bacterial DNA extracted according to example 1 (lane 2), according to example 2 (lane 3) and according to example 3 (lane 4).

All patents applications, publications, or other references that are listed herein are hereby incorporated by reference.

The problem that the invention proposes to solve is therefore to develop a simple method for extracting, purifying, separating and extracting DNA fragments which are large in size, in particular greater than 300 kB, of non-cultivatable organisms and mainly bacteria. The obtaining of these DNAs which are large in size, purified and extracted in this way, is an indispensable condition for producing genomic and metagenomic DNA libraries which are adequate in the field of application.

Another objective of the invention is to provide a method which makes it possible to purify, separate and extract the target DNA free of any DNA contamination, in particular eukaryotic DNA or degraded extracellular DNA, for the purpose of preparing adequate libraries.

Another problem that the invention proposes to solve is to be able to apply the method developed to many environmental samples, and in particular, but in a nonlimiting manner, plants, insects, for example arthropods, mollusks, sponges, crustacea, Platyhelminthes, nematodes, bioreactors such as biofilms, fermentors, activated sludge and, more generally, aquatic media, but also animal (for example pig manure, rumen bolus) or human biological samples.

As regards the latter environment, document EP-A-0 939 118 describes a method for directly extracting DNA and RNA from feces, according to which the material is mixed in detergent medium before being subjected to the actual extraction of the DNA and of the RNA in a suitable solvent. No indication is given regarding the size of the DNA extracted, but the extraction of small fragments may be expected. In addition, and as above, contamination of the target DNA in eukaryotic DNA is observed.

The objective of the invention is therefore to provide a method for indirectly extracting the target DNA of non-cultivatable organisms contained in environmental samples, which makes it possible to obtain specific DNA fragments greater than 300 kB in size able to be cloned by the usual techniques known to those skilled in the art. In fact, this DNA will make it possible to constitute adequate DNA libraries which are more representative of the genomes or metagenomes considered.

To do this, the invention provides a method for indirectly extracting target DNA greater than 300 kB in size of non-cultivatable organisms contained in an environmental sample, according to which:

said sample is ground in liquid medium;

the ground material obtained is recovered;

the organisms are separated from the rest of the ground material by sedimentation on a cushion with a density greater than 1;

the isolated organisms at the surface of the cushion are recovered and are embedded in a block of agarose;

the DNA is extracted by lysis in the block of agarose;

the block is placed in an agarose gel which is subjected to at least one alternating field electrophoresis;

finally, the DNA strands extracted are recovered.

The applicant has noted that prior separation of the organisms from the rest of the ground material by sedimentation on a density cushion, and then lysis of these organisms directly in a block of agarose, makes it possible to separate and to obtain, by carrying out a pulsed field electrophoresis, DNA fragments greater than 300 kB in size. In fact, proceeding in this way makes it possible to never directly handle the DNA, thus avoiding any degradation due to enzymatic or mechanical constraint phenomena. In addition, the method of the invention allows selective and considerable purification of the DNA fragments being sought by removing the inevitable DNA losses linked to conventional purification methods (organic extractions, precipitations, ion exchange methods, etc.). Furthermore, so as not to impair the integrity of the DNA fragments, particularly in the case of DNA fragments which are large in size, or so as not to affect subsequent cloning efficiencies, the steps for preparing the DNA fragments are advantageously carried out without any intercalating agents (ethidium bromide, etc.) or any visualization under UV.

As regards the step for separating the organisms from the rest of the ground material, the density cushion will be chosen as a function of the density of the organism which must be separated from the other constituents of the ground material. Thus, when this involves separating the bacterial fraction from the rest of the organelles and debris, it is known that this has, depending on the species, a density which can range from 1 to 1.4. Depending on the case, the density of the cushions used will be adjusted in order to optimize the separation of the bacterial fraction from the other constituents of the ground material.

In a preferred embodiment, the step for separating the organisms will be followed by a step of centrifugation on an isopycnic density gradient, thus making it possible to separate the organisms as a function of their density.

Moreover, and according to an advantageous characteristic of the method of the invention, the sedimentation step is accelerated by centrifugation.

The alternating field electrophoresis technique is completely known to those skilled in the art, and more particularly described in document U.S. Pat. No. 5,135,628 and in the review "le technoscope de biofutur" [The biofuture technoscope] No. 127 of October 1993, such that the principle thereof will not be reiterated further.

Advantageously, the DNA strands separated and purified at the end of the alternating field electrophoresis step (hereinafter referred to as first electrophoretic migration) are subjected to an enzymatic restriction step followed by at least one alternating field electrophoresis (second electrophoretic migration). In this case, the first electrophoretic migration is used to extract the DNA fragments which are large in size and to separate them from the cell debris. In practice, the areas of gel containing the DNAs of desired size (for example greater than 300 kB) are cut out in a preparative mesure. The DNA fragments embedded in the blocks of agarose thus obtained are then subjected to enzymatic restriction directly in the block of agarose or, optionally, after extraction of the DNA from the agarose. The blocks of agarose containing the digested DNAs are then again placed in an agarose gel and are then subjected to at least one electrophoretic migration making it possible to separate and purify the digested DNAs.

In a first embodiment, the enzymatic restriction step is followed by two rounds of alternating field electrophoresis (second and third electrophoretic migration, respectively).

In practice, the blocks of agarose containing the digested DNA fragments are placed off-center in a second gel. The gel is placed in the alternating field electrophoresis tank successively in one direction (second migration) and then in the opposite direction (third migration). During the second electrophoretic migration, of short duration, placing the gel in a homogeneous electric field makes it possible to bring the small DNA fragments out of the gel, while keeping the large fragments in the gel. During the third migration, the gel is placed in the other direction and the large fragments can be separated according to their size. The applicant has noted that the double migration makes it possible to remove the fragments small in size entangled in the DNA fragments of the desired size.

In a second embodiment, the enzymatic restriction step is followed by three rounds of alternating field electrophoresis (second, third and fourth electrophoretic migration, respectively).

In practice, after the second electrophoretic migration, a band of agarose containing the digested DNA fragments of the desired size is cut out and put back in place, in the opposite direction, in a new, strictly identical gel. This gel is subjected to the same electrophoretic migration (third migration). Since the mobility specific to each DNA fragment, at all points of the area of agarose cut out, is conserved between the second and third migration, all the DNA fragments ultimately migrate toward the same concentrated area of the gel. The applicant has noted that the DNA fragments small in size entangled in the DNA fragments of the desired size (contained in the area of gel in which the DNA is concentrated) can be removed by subjecting this area of gel or this gel to a fourth alternating field electrophoretic migration in a direction identical to that of the third migration. This final migration is characterized by parameters which separate very little and which affect only the small DNA fragments.

Finally, and in the two embodiments, the DNA strands thus prepared (purification, digestion, selection, concentration) are recovered by techniques known to those skilled in the art, such as, for example, electroelution (for instance with the systems marketed by the company Biorad and Schleicher & Schuell), digestion of the agarose (using commercially available enzymes such as the β-agarase marketed by New England Biolabs or the Epicentre Technologies gelase, and according to the suppliers' instructions), and use of commercially available kits (Nucleo Trap DNA extraction Kit, Clontech; Gene Clean turbo spin BIO101) known to those skilled in the art. In other words, the combination of grinding, differential sedimentation, lysis of the block of agarose and successive alternating field electrophoresis steps makes it possible, to purify the DNA by removing all debris inherent to lysis of the cells embedded in the block, to separate the DNA as a function of its size to obtain concentrated DNA with the desired size.

In other words, the method developed in the invention makes it possible not only to purify, separate and visualize the DNA by gel electrophoresis, but also to recover this DNA while precisely controlling the size of the DNAs required for the subsequent cloning steps. The DNA thus obtained can be used as a matrix in order to be cloned by conventional techniques. These techniques can use either enzymatic restriction (sticky ends), or blunt-ended cloning or the synthesis of complementary homopolymeric tails on the insert and the vector, as described in J. Sambrook, E F. Fritsch and T. Maniatis, 1989, Molecular Cloning: a laboratory manual II edition, Cold Spring Harbor Laboratory, N.Y. The major drawback of enzymatic restriction is the selection engendered by the recognition sites of the restriction enzymes used. In fact, restriction unequally affects DNA fragments with variable GC levels. Blunt-ended ligation and synthesis of complementary homopolymeric tails makes it possible to avoid any selection of the DNA fragments.

In addition, many cloning or expression vectors have already been described in the prior art. These are, in a nonlimiting manner, widely marketed plasmids, phagemids such as, for example, (pBluescript SK), phage-derived vectors such as, for example, those marketed by the company Stratagene (Lambda DASH II and ZAP II), cosmids such as, for example, those marketed by Stratagene (SuperCos and pWE15) and Epicentre TEBU (pWED cosmid cloning kit), fosmids such as that described by U. J. Kim, H. Shizuya, P. J. de Jong, B. Birren and M. I. Simon, 1992—Stable propagation of cosmid sized human DNA inserts in a F factor based vector, Nucleic Acids Research 20(5): 1083–1085), PAC artificial chromosomes as described by P. A. Ioannou, C. T. Amemiya, J. Games, P. M. Kroisel, H. Shizuya, C. Chen, M. A. Batzer and P. de Jong, 1994—A new bacteriophage P1-derived vector for the propagation of large human DNA fragments, Nature Genetics, 6: 84–89, BACs as described by H. Shizuya, Bruce Birren, Ung-Jin Kim, Valeria Mancino, Tatiana Slepak, Yoshiaki Tachiiri and Melvin I. Simon, 1992—A bacterial cloning system for cloning large human DNA fragments, Proc. Natl. Acad. Sci., 89: 8794–8797) and YACs as described by Z. Larin, A. P. Monaco and H. Lehrach, 1991—Yeast artificial chromosome libraries containing large inserts from mouse and human DNA, Proc. Natl. Acad. Sci., 88: 4123–412. The vectors, techniques for preparing the vectors and cloning techniques have been the subject of many studies and are already widely described.

As already mentioned, one of the objectives of the method of the invention is that it may be adapted to a large variety of environments.

In the remainder of the description and in the claims, the expression "non-cultivatable organism" denotes any organism which cannot be grown on synthetic medium, such as in particular, but in a nonlimiting manner, prokaryotes such as bacteria (endosymbiotic or parasitic bacteria), archaebacteria or protists.

Of course, the method of the invention makes it possible, at the same time, to isolate the cultivatable organisms since the sedimentation on a cushion does not make it possible to distinguish the cultivatable bacteria from the non-cultivatable bacteria.

Similarly, the term "environmental sample" denotes both the soil and sediments and plants, insects, for example arthropods, mollusks, sponges, crustacea, Platyhelminthes, nematodes, bioreactors such as biofilms, fermentors, activated sludge and, more generally, aquatic media, but also animal (for example pig manure, rumen bolus) or human biological samples and, advantageously, any fraction obtained from these environments having a quantitative advantage (high bacterial concentration) or qualitative advantage (specificity of the bacteria community or population).

In the remainder of the description, the method which is the subject of the invention is more particularly described in relation to the extraction of DNA of the non-cultivatable bacterial flora contained in drosophila, soil and feces of human origin.

Thus, in a first embodiment, the environmental sample is an insect. In fact, endosymbiotic bacteria, and in particular those of the genus *Wolbachia*, are also known to be among the non-cultivatable organisms which are of potential interest. This type of endosymbiont is present in a large number of invertebrates, and especially of arthropods, in particular in drosophila. These bacteria are also found in mollusks. More particularly, the bacteria of the genus *Wolbachia* are preferentially located in the reproductive organs of insects, as described by J H. Werren, 1997. Biology of *Wolbachia*. Annual Review of Entomology. 42, 587–609. To extract exclusively the bacterial DNA rather than the nuclear DNA, the method of the invention is carried out using unfertilized drosophila eggs, therefore eggs from virgin females.

Moreover, the applicant has noted that, in the case of insects and more particularly of drosophila, controlled grinding followed by filtration and then centrifugation makes it possible to optimize the subsequent separation of the major bacterial fraction from the rest of the ground material.

In a second embodiment of the invention, the environmental sample is a soil sample or a granulometric subfraction as described, for example, by T. Hattori, 1988. Soil aggregates as microhabitats of microorganisms. Biology and Fertility of Soils. 6, 189–203, and by L. Jocteur-Monrozier, J N Ladd, R W Fitzpatrick, R. C. Foster and M. Raupach, 1991. Components and microbiomass content of size fractions in soils of contrasting aggregation. Geoderma, 49, 37–62.

According to an advantageous but nonlimiting example of implementation, the soil used is a superficial soil layer fraction.

In a first embodiment, the soil sample can preferentially but not exclusively be ground in a buffer containing sucrose at a concentration equal to 30 millimole per liter, EDTA at a concentration equal to 25 millimole per liter and TES at a concentration equal to 50 millimole per liter. The term "grinding" is intended to mean any method which makes it possible to disperse the bacterial cells from the other constituents.

Moreover, the grinding step comprises successively:
a first vigorous grinding of the sample;
a washing centrifugation;
taking the pellet up in a physiological buffer solution;
two additional rounds of vigorous grinding.

Of course, the grinding and centrifugation conditions are dependent on the mass of starting material used. As regards more particularly the centrifugation, it is carried out at a rate of between 5 000 and 10 000 rpm, advantageously 6 000 rpm, for 5 to 15 minutes, advantageously 10 minutes.

The applicant has noted that, most surprisingly, this series of steps makes it possible to optimize the subsequent separation of the non-cultivatable organism from the rest of the ground material.

In a second embodiment, the soil sample is ground in a 0.8% NaCl buffer solution.

In a third embodiment, the environmental sample is in the form of a human or animal biological sample. In an advantageous embodiment, the biological sample consists of feces of human origin.

In order to make it possible to separate the intestinal flora from the solid material, the grinding is followed by a filtration step. As previously, the term "grinding" is intended to mean any system of dispersion of the microorganisms.

As regards the aquatic media, it may be necessary to preconcentrate the sample, depending on its initial volume. In particular, a preferred approach would be the use of continuous flow centrifugation techniques as described, for example, in Centrifugation: A practical approach (2nd). 1984. Eds., D. Rickwood & B. D. Hames (IRL Press, Oxford, Washington D.C.).

For all these environmental samples described in a non-limiting manner, the non-cultivatable organisms are separated from the rest of the ground material, as already mentioned, by sedimentation on a cushion with a density greater than 1. In practice, a solution of Nycodenz, Percoll, Ficoll, Metrizamide or Iodixanol is used, as desired, which is placed at the bottom of a tube, under the ground material. Differential sedimentation is established at the bottom of the tube for the very dense particles and, in an ordered manner, on the cushion for the others. As already mentioned, this sedimentation can be accelerated by centrifugation.

According to an advantageous characteristic of the method of the invention, the fraction containing the organisms recovered at the end of the sedimentation step is subjected to two subsequent, successive centrifugation steps for washing with water, at a rate of between 6 000 and 10 000 rpm and a temperature of between 3 and 5° C., advantageously 4° C.

Moreover, in order to make it possible to extract a maximum of DNA, the mixture consisting of the cultivatable and non-cultivatable organisms embedded in a block of agarose at the end of the two subsequent centrifugation steps is subjected to two successive rounds of lysis:
first of all, a first lysis in a buffer based on lysosyme and achromopeptidase;
then, a second lysis in a buffer based on 1% lauryl sarcosyl and proteinase.

In order to allow separation of the DNA fragments, the block of agarose incorporating the lysed organisms is subjected to agarose gel alternating field electrophoresis.

In practice, the agarose gels are ultrapure, low melting point gels (high molecular grade) advantageously at a concentration of 0.8% (0.7 to 1.2%). Preferentially, but in a nonlimiting manner, the electrophoretic migrations are carried out under a voltage of 150V for varying periods of time of the order of 10 to 24 hours. Pulse variation (for example from 1 to 5 seconds up to 10 to 25 seconds) makes it possible to obtain optimal separations according to the size of the desired DNA fragments, and to control and optimize the separation of the desired DNA fragments according to size.

As already mentioned and in a preferred embodiment, the DNA strands separated and purified at the end of the alternating field electrophoresis step (first electrophoretic migration) are subjected to an enzymatic restriction step followed by at least one electrophoresis (second electrophoretic migration).

In this case, the first electrophoretic migration is used to extract the DNA fragments which are large in size and to separate them from the cell debris. Highly separating electrophoretic conditions may advantageously be used, such as, for example, pulses of 10 to 25 seconds for 20 hours (150V). This preparative migration makes it possible to recover DNA fragments greater than 300 Kb.

The DNA greater than 300 Kb in size contained in the agarose is cut out and subjected to enzymatic restriction in the agarose. The amounts of enzymes used and also the application time depend in particular on the specific activity of the enzyme and on the amount of DNA present.

In a first embodiment, two rounds of electrophoresis are carried out.

In this case, the blocks of agarose, containing the digested DNAs, are again placed in an agarose gel and subjected to one or more rounds of alternating field electrophoresis in order to separate and purify the digested DNAs, in the same gel. Advantageously, the digested DNAs are subjected to two rounds of alternating field electrophoresis corresponding to a double electrophoretic migration. In a homogeneous and constant electric field, the gel is alternately placed in one direction and in the strictly opposite direction. During the first electrophoretic migration, the direction of the electric field makes it possible to bring the small DNA fragments out of the gel. In fact, the off-center placement of the blocks of agarose makes it possible to bring the small DNA fragments out, on the shortest side, while at the same time keeping the large fragments in the gel. In a second migration, the gel is placed in the other direction and the large DNA fragments can thus be separated according to their size. The conditions of the first migration are preferentially 10/25 seconds for 4 hours. The conditions of the second migration are preferentially 10/25 seconds for 20 hours.

In a second embodiment, three rounds of electrophoresis are carried out.

In this case, a second separating electrophoretic migration, in a gel consisting of 100 ml of 0.8% ultrapure, low melting point agarose (Biorad), makes it possible to separate the digested DNA fragments according to their size (using 5/15 seconds for 17 h under a voltage of 150V).

The DNA fragments of the desired size are concentrated by recovering the block of agarose and subjecting it to a return migration (third migration) (placing the block of agarose in the opposite direction on a new gel). The gel and the electrophoretic migration conditions should be absolutely identical.

A final electrophoretic migration (fourth migration) is carried out in order to eliminate the small DNA fragments entangled in the DNA fragments of desired size. This electrophoresis is performed under conditions which separate very little, affecting only the small fragments (pulses of 1/5 seconds for 10 hours under a voltage of 150V).

The fact of maintaining DNA fragments in agarose and of using neither intercalating agents nor UV visualization makes it possible to preserve the quality and integrity of DNA which is large in size.

As already mentioned, the invention also relates to the DNA greater than 300 kB in size which can be obtained by the method described above. The DNA thus obtained may, depending on the various embodiments of the method, have "sticky" ends (when it has been the subject of enzymatic restriction), "blunt" ends (when it has been the subject of mechanical cleavage and enzymatic repair of the Klenow or T4 DNA polymerase type, for example) or, finally, homopolymeric tails (when it has been the subject of treatment with the terminal transferase enzyme). All these techniques are already widely documented (Current protocols in molecular biology, Eds. F. M. Ausubel, R. Brent, R. E. Kingston, D. D. Moore, J. G. Seidman, J. A. Smith and K. Struhl, published by Greene Publishing Associates and Wiley-Interscience. This DNA can be used in any molecular biology experiment, such as, for example, and in a nonlimiting manner, for the construction of DNA libraries using all the suitable cloning techniques known to those skilled in the art.

Given the purity and the size of the DNA, all types of cloning or expression vector can be used. For example, and in a nonlimiting manner, these vectors are of the following type:

Phagemide: pBluescript SK+ (pSK+) (A. Henne, R. Daniel, R. A. Schmitz and G. Gottschalk—Construction of environmental DNA libraries in *Escherichia coli* and screening for the presence of genes conferring utilization of 4-hydroxybutyrate, Applied and Environmental Microbiology, 65: 3901–390

Phage-derived vectors: lambda ZAPII M. T. Cottrell, J. A. Moore and D. L. Kirchman, 1999—Chitinases from uncultured marine microorganisms, Applied and Environmental Microbiology, 65: 2553–2557

Cosmid vector pCPP47; D. W. Bauer and A. Collmer, 1997—Molecular cloning, characterization, and mutagenesis of a pel gene from *Pseudomonas syringae* pv. *Lachrymans* encoding a member of the *Erwinia chyrsanthemi* PelADE family of pectate lyases, Molecular Plant-Microbe Interactions, 10: 369–379

Fosmid pFOS1 (vector described by U. J. Kim, H. Shizuya, P. J. de Jong, B. Birren and M. I. Simon, 1992—Stable propagation of cosmid sized human DNA inserts in an F factor based vector, Nucleic Acids Research 20(5): 1083–1085) J. L. Stein, T. L. Marsh, K. Y. Wu, H. Shizuya and E. deLong, 1996—Characterization of uncultivated prokaryotes: isolation and analysis of a 40-kilobase-pair genome fragment from a planktonic marine archaeon, Journal of Bacteriology, 178: 591–599

P1 bacteriophage-derived PAC vector (pCYPAC-1), P. A. Ioannou, C. T. Amemiya, J. Garnes, P. M. Kroisel, H. Shizuya, C. Chen, M. A. Batzer and P. de Jong, 1994—A new bacteriophage P1-derived vector for the propagation of large human DNA fragments, Nature Genetics, 6: 84–89

BAC vector pBeloBAC11 (pSK+) (vector described by H. Shizuya, Bruce Birren, Ung-Jin Kim, Valeria Mancino, Tatiana Slepak, Yoshiaki Tachiiri and Melvin I. Simon, 1992—A bacterial cloning system for cloning large human DNA fragments, Proc. Natl. Acad. Sci., 89:

8794–8797); H. Shizuya, B. Birren, U. -J. Kim, V. Mancino, T. Slepak, Y. Tachiiri and M. Simon, 1992—Cloning and stable maintenance of 300-kilobase-pair fragments of human DNA in *Escherichia coli* using an F-factor-based vector, Proceeding of National Academy of Science, 89, 8794–8797; S. -S. Woo, J. Jiang, B. S. Gill, A. H. Paterson and R. A. Wing, 1994—Construction and characterization of a bacterial artificial chromosome library of *Sorghum bicolor*, Nucleic Acids Research, 22, 4922–4931; M. R. Rondon, S. J. Raffel, M. R. Goodman and J. Handelsman, 1999—Toward functional genomics in bacteria: Analysis of gene expression in *Escherichia coli* from a bacterial artificial chromosome library of *Bacillus cereus*, Proceeding of National Academy of Science, 96: 6451–6455.

YAC vector pYAC4, Z. Larin, A. P. Monaco and H. Lehrach, 1991—Yeast artificial chromosome libraries containing large inserts from mouse and human DNA, Proceeding of National Academy of Science, 88: 4123–4127.

The ligation between the various possible vectors and the DNA fragments may be carried out conventionally as described by the suppliers, depending on the type of enzyme used, such as, for example (T4 DNA ligase, companies Roche or Life Technologies; Fast Link DNA ligation Kit, company Epicentre Technologies) or in gel as described, for example, by the company Epicentre Technologies in the pWEB Cosmid Cloning Kit.

The transformation or the encapsidation (depending on the vector used) have been widely described, such as, for example, in Current Protocols in Molecular Biology, Eds. F. M. Ausubel, R. Brent, R. E. Kingston, D. D. Moore, J. G. Seidman, J. A. Smith and K. Struhl; published by Greene Publishing Associates and Wiley-Interscience, and also in the suppliers' instructions.

Finally, the invention relates to the DNA libraries thus consisting of the DNA fragments obtained by the method described above and in a nonlimiting manner, for their use in molecular, phenotypic or chemical screening.

The invention and the advantages which ensue therefrom will emerge more clearly from the following examples of implementation supporting the attached figures.

EXAMPLE 1

Extraction of DNA of Endosymbiotic Bacteria of the Wolbachia Type from Drosophila Eggs I—Starting Material 10 to 20 000 unfertilized eggs from *Drosophila simulans* virgin females are dissolved in approximately 500 µl of 0.8% NaCl. The use of unfertilized eggs is essential since it makes it possible to extract mainly the bacterial DNA with a minimum load of nuclear DNA.

II—Grinding of Material

The grinding is carried out in a controlled manner in a 1.5 ml microtube using a sterile polypropylene plunger and adding sterile fontainebleau sand. The grinding comprises the following steps:
    grinding in ice for 2 minutes;
    briefly centrifuging at 4 000 rpm at a temperature of 4° C.;
    recovering the turbid supernatant in a 38 ml Kontron Ultraclear tube;
    resuspending the pellet with 500 µl of 0.8% NaCl;
    repeating steps a) to d) on the same sample;
    taking up the supernatants from the 3 rounds of grinding, in an ultraclear tube;
    taking up the final pellet of ground material and filtering through sterile cotton wool with 0.8% NaCl, qs 20 ml;
    recovering the filtrate and adding it to the supernatant of f/.

III—Carrying Out the Density Gradient Sedimentation Step

A 30% weight/volume NYCODENZ solution is prepared (15 g in 50 ml of ultrapure water) corresponding to a density of the order of 1.16. A 10 ml cushion of NYCODENZ is then put in place in the ultraclear tube, using a pipette, under the suspension derived from the grinder. The sedimentation is then accelerated for 30 minutes at a temperature of 4° C. by centrifugation at 9 000 rpm using a swing-out bucket rotor, with braking, of the TST 2838 type (KONTRON).

IV—Treatment of the Bacterial Fraction

At the end of the sedimentation step, several successive layers are observed in the ultraclear tube by optical microscopy, from top to bottom:
    layer 1: turbid fraction with fine debris in suspension and points visible under the microscope corresponding to bacteria and mitochondria;
    layer 2: translucent fraction with points visible under the microscope;
    layer 3: whitish fraction with a large number of points comprising mainly bacteria, and also mitochondria;
    layer 4: translucent fraction with no structure visible under the microscope corresponding to the dense cushion of NYCODENZ;
    layer 5: a whitish pellet corresponding to the debris not retained by the filtration through cotton wool.

4 to 5 ml of the bacterial fraction are recovered from layer 3 using a sterile tip. The volume recovered is then taken up with 20 ml of ultrapure water. Further centrifugation is then carried out at a rate of 9 000 rpm at a temperature of 4° C. for 15 minutes with braking, to pellet the bacteria. It is observed that the points contained in layers 1 and 2 cannot be pelleted, which suggests that they comprise degraded mitochondria and bacteria. The supernatant obtained at the end of the first centrifugation step is discarded and the bacterial pellet is taken up with approximately 1.5 ml of ultrapure water. A further washing centrifugation is then carried out at 9 000 rpm at 4° C. for 5 minutes. Finally, the supernatant is discarded and the pellet is stored at −20° C.

V—Preparation of the Blocks of Agarose and Lysis

The bacterial pellet after NYCODENZ is taken up with 100 µl of Tris EDTA, $TE_{10,1}$, [pH 8.0]. This bacterial suspension is mixed vol/vol with 100 µl in a block of low melting point agarose (BIORAD) equilibrated at 55° C. The block is poured into molds (BIORAD plug mold) in a proportion of 100 µl per mold. The molds are kept on ice for 20 minutes. The plugs are carefully removed from the mold and are taken up and placed in a tube, where the lysis is carried out.

First Lysis Step

Each block is taken up in a 5 ml sterile Venoject tube with 3 ml of lysis buffer 1 ($TE_{10,1}$, [pH 8.0], 5 mg/ml lysosyme, 0.5 mg/ml achromopeptidase). Incubation is carried out for 2 hours at 37° C.

Second Lysis Step

The lysis buffer 1 is removed. Each block is taken up in 3 ml of lysis buffer 2 ($TE_{10,1}$, [pH 8.0], 1% lauryl sarcosyl, 100 µg/ml proteinase K. Incubation is carried out for 2 hours at 55° C. The plugs are rinsed successively three times for 30 minutes, in 3 ml of $TE_{10,1}$, [pH 8.0].

VI—Alternating Field Electrophoresis

Each of the blocks is placed in the wells of an agarose gel consisting of 100 ml of 0.8% low melting point agarose (BIORAD). The agarose gel is subjected to alternating field electrophoresis using a Chef DR II Pulsed Field Electrophoresis System device (BIORAD). A migration buffer consisting of Tris Borate EDTA (0.5x) is used. The electrophoretic migration is carried out under a voltage of 150V for 22 hours. Pulses of 10 to 25 seconds make it possible to obtain two alternating electric fields.

The size of the DNA is visualized and then pinpointed by staining the part of the gel containing the size marker and a double of the migrated DNA with ethidium bromide. Thus, the DNA subsequently used is never damaged by using an intercalating agent or UVs. After cutting out from the gel, staining in ethidium bromide and visualization on the UVs makes it possible to verify the size of the DNA fragments effectively recovered.

The migration profile of the DNA extracted (lane 2) is represented on the attached FIG. 1, lanes 1 and 5 representing the size marker marketed by the company BIOLABS, under the trade mark Lambda ladder PFG Marker and low range PFG marker.

As shown in FIG. 1, the bacterial DNA fragment is greater than 300 kB in size. The fragment between 200 and 250 kB in size is probably DNA originating from the drosophila host. This clearly demonstrates the ability of the method to separate the target DNA from the rest of the DNA, first of all due to the grinding and to the differential sedimentation on a density gradient (genomic DNA), and then due to the alternating field electrophoresis (mitochondrial DNA).

VII Recovery of the DNA

This is carried out using a gelase (Epicentre TEBU), digesting the agarose according to the indications provided by the supplier.

The agarose band containing the DNA is incubated in three volumes of the reaction buffer for the enzyme (1 hour at ambient temperature);

the buffer is removed and the agarose band is incubated for 5 minutes at 70° C.; the agarose thus liquefied is equilibrated at a temperature of 45° C. for 5 minutes;

an amount of enzyme consisting of 1 to 3 units of gelase is added and the entire mixture is incubated for 1 hour at 45° C. until complete digestion of the agarose (the digestion is verified by plunging the sample tube into ice);

either the DNA is used directly in the gelase reaction medium, for enzymatic reactions or any other manipulation, or the DNA is precipitated with ammonium acetate as described by the supplier (Epicentre Technologies).

EXAMPLE 2

Extraction of the Bacterial Flora from Soil

I—Starting Material 7.5 g of soil are taken up in 50 ml of a buffer solution comprising 30 mM sucrose, 25 mM EDTA and 50 mM TES.

II—Grinding of Material a) the material is ground in a grinding bowl using a WaringBlender for 1 minute at maximum power;

b) the ground material is taken up in a 50 ml Falcon tube and centrifuged at 6 000 rpm at 10° C. for 10 minutes;

c) the supernatant is removed and the pellet is taken up with 50 ml of 0.8% NaCl;

d) 2 rounds of grinding for 1 minute with a WaringBlender at maximum power are carried out, with a 5 minute pause between the two in ice (cooling of the ground soil material);

e) the ground material is taken up in a 50 ml Falcon tube and kept in ice.

III—Carrying Out the Density Cushion Sedimentation

A 60% weight/volume solution of NYCODENZ is prepared (30 g in the final volume of 50 ml of ultrapure water), corresponding to a density of 1.32. A 10 ml cushion of NYCODENZ is then put in place in the ultraclear tube, using a pipette, under the suspension derived from grinding. The sedimentation is then accelerated for 10 minutes at a temperature of 4° C. by centrifugation at 10 000 rpm using a swing-out bucket rotor, without braking, of the TST 2838 type (KONTRON).

IV—Treatment of the Bacterial Fraction

At the end of the sedimentation step, several successive layers are observed in the ultraclear tube, from top to bottom:

layer 1: translucent aqueous fraction;
layer 2: whitish bacterial fraction;
layer 3: translucent cushion of NYCODENZ;
layer 4: soil sedimentation 4 to 5 ml of the bacterial fraction of layer 2 are recovered using a sterile tip. The nucleases are then inactivated by incubating the bacterial fraction at 65° C. for 10 minutes. The volume recovered is taken up with 20 ml of ultrapure water. Centrifugation is then carried out using a bucket rotor, in order to pellet the bacteria, at a rate of 9 000 rpm at a temperature of 4° C. for 20 minutes with braking. The supernatant is removed and the bacteria pellet is taken up with approximately 1.5 ml of ultrapure water. A further washing centrifugation is then carried out at 9 000 rpm at 4° C. for 5 minutes. Finally, the supernatant is removed and the pellet is stored at −20° C.

V—Preparation of the Blocks of Agarose and Lysis

Example 1 is repeated.

VI—Alternating Field Electrophoresis

Each of the lysed blocks is placed in the wells of an agarose gel consisting of 100 ml of 0.8% low melting point agarose (BIORAD). The agarose gel is subjected to alternating field electrophoresis using a Chef DR II Pulsed Field Electrophoresis System device (BIORAD) in order to perform a preparative electrophoresis. A migration buffer consisting of Tris Borate EDTA (0.5x) is used. The preparative electrophoretic migration is carried out under a voltage of 150V for 20 hours with pulses of 10 to 25 seconds.

In the same way as in example 1, the DNA extracted at the end of the first migration is visualized and pin-pointed on the gel (see lane 3 of FIG. 1).

The blocks of agarose (approximately 100 mg) are then recovered and then subjected to enzymatic restriction with HindIII:

incubation for 1 hour in 500 µl of enzyme buffer (1x) at 4° C.;

replacement of the buffer with 250 µl of the same buffer with 10 U of enzyme;

incubation for 2 hours in ice;

transfer at 37° C. and incubation for 1 hour.

Figure 2A:
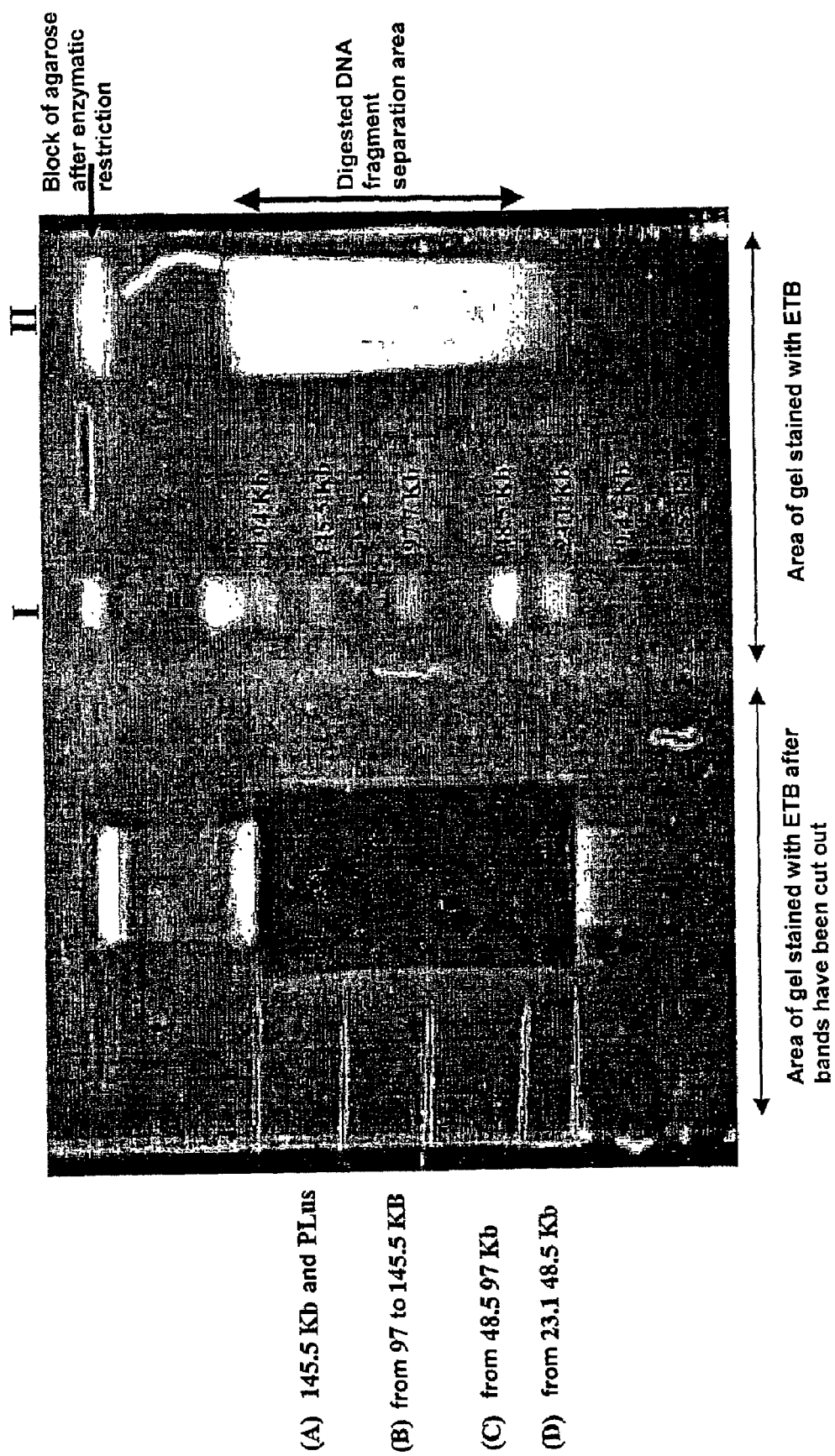
FIG. 2 represents the migration profile of bacterial DNA extracted according to example 2, at the end of the second migration (2A) and of the third migration (2B).
Figure 2B:
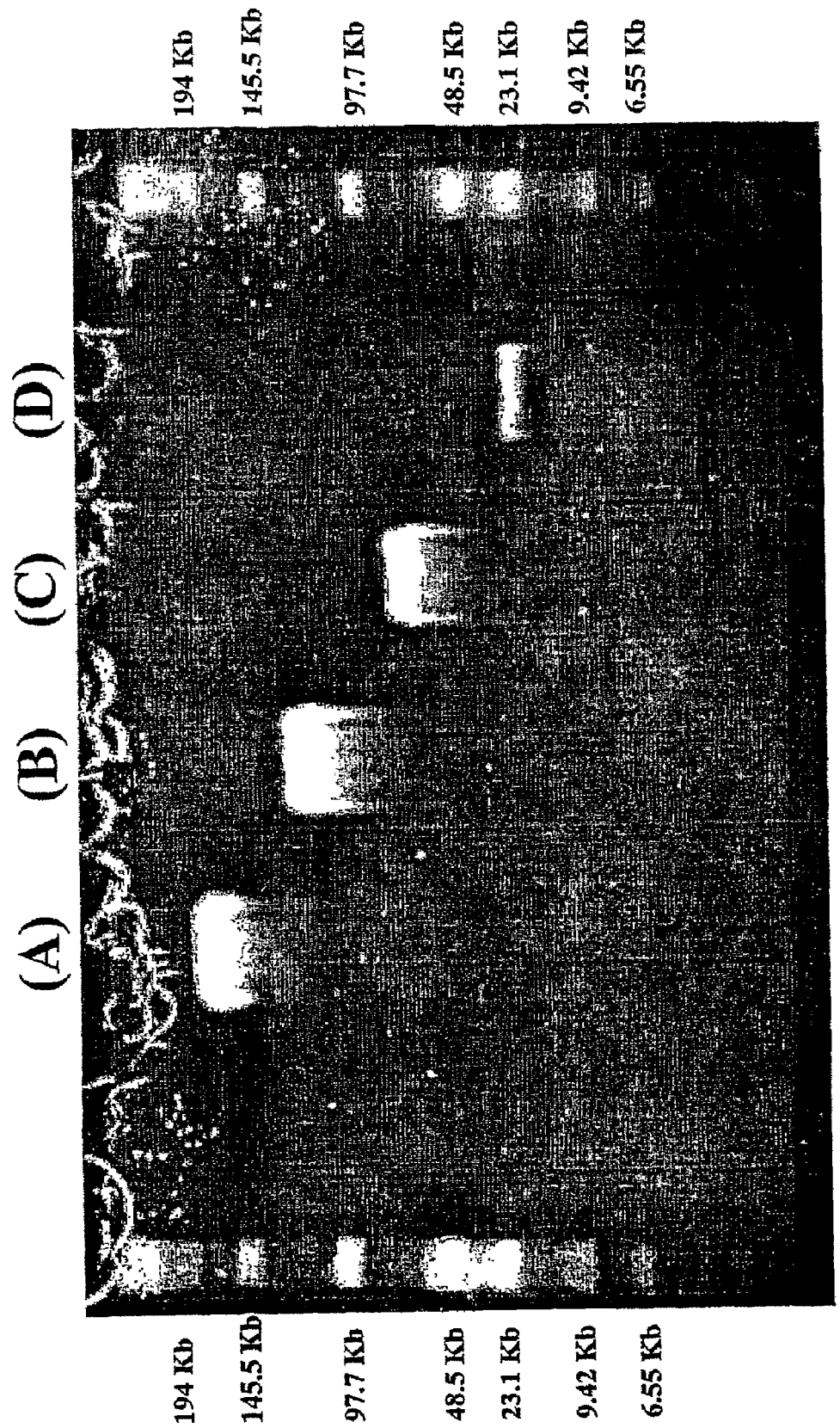

The block of agarose containing the digested DNA is taken up and placed in an agarose gel consisting of 100 ml of 0.8% low melting point agarose (Biorad). A second pulsed field electrophoretic migration is then carried out under a voltage of 150V, at 5/15 seconds, for 17 hours. The digestion "smear" is located (FIG. 2A), as described above, and areas of gel are cut out according to the desired size. The blocks are then placed in the opposite direction in a new, strictly identical gel and subjected to a third pulsed field electrophoretic migration under strictly identical conditions (concentration). The DNA fragments contained in the various bands cut out and concentrated by the third migration are visualized (FIG. 2B). The concentrated DNA fragments are then subjected to a fourth electrophoretic migration under a voltage of 150V, 1/5 seconds, for 10 hours.

VII—Recovery of the DNA
Example 1 is repeated

EXAMPLE 3

Extraction of Intestinal Bacterial Flora

I—Starting Material
3 g of stools are taken up in 50 ml of 0.8% NaCl.

II—Grinding of Material
The grinding is carried out using a sterile Teflon Potter homogenizer in a borosilicate glass cylinder;
a) grinding for 2–5 minutes in ice;
b) should the grinding with the Potter homogenizer not be sufficient, the material is subjected to very rapid grinding in a WaringBlender (5–10 seconds);
c) the ground material is filtered through sterile gauze.

III—Carrying Out the Density Cushion Sedimentation
A 30% weight/volume NYCODENZ solution is prepared (15 grams in a final volume of 50 ml of ultrapure water), corresponding to a density of 1.16. A 10 ml cushion of NYCODENZ is then put in place in the ultraclear tube, using a pipette, under the suspension derived from the grinding. The sedimentation is then accelerated for 30 minutes at a temperature of 4° C. by ultracentrifugation at 9 000 rpm.

IV—Treatment of the Bacterial Fraction
At the end of the sedimentation step, several successive layers are observed in the ultraclear tube, from top to bottom:
layer 1: highly colored aqueous fraction;
layer 2: whitish bacterial fraction;
layer 3: translucent cushion of NYCODENZ;
layer 4: pellet corresponding to the dense organic debris.
Approximately 4 to 5 ml of the bacterial fraction contained in layer 2 are recovered using a sterile tip. The volume recovered is taken up with 20 ml of the ultrapure water. Centrifugation with a bucket rotor is then carried out, in order to pellet the bacteria, at a rate of 9 000 rpm, at a temperature of 4° C., for 20 minutes, with braking. The supernatant is removed and the bacterial pellet is taken up with approximately 1.5 ml of ultrapure water. A further washing centrifugation is then carried out at 6 000 rpm and 4° C. The supernatant is removed and the pellet is stored at −20° C.

V—Preparation of the Agarose Blocks and Lysis
Example 2 is repeated.

VI—Alternating Field Electrophoresis
Example 2 is repeated.
The attached FIG. 1 represents the migration profile of the extracted DNA (lane 4). It is observed that the size of the extracted DNA fragment is greater than 300 kB.

VII—Recovery of the DNA
Example 1 is repeated.

What is claimed is:

1. A method for extracting DNA from organisms contained in sample, said method comprising:
    (a) grinding said sample in liquid medium;
    (b) recovering the ground material obtained in (a);
    (c) isolating said organisms from the ground material by sedimentation using a density gradient solution with a density greater than 1;
    (d) embedding the organisms isolated in (c) in a block of agarose;
    (e) releasing DNA of said organisms by lysis of said organisms in the block of agarose;
    (f) placing said block in a well of an agarose gel and subjecting said block to a first electrophoretic migration comprising exposure to at least one alternating field electrophoresis; and
    (g) recovering DNA from the agarose gel.

2. The method of claim 1, further comprising the step:
    (h) subjecting the DNA from (g) to an enzymatic restriction step followed by a second electrophoretic migration in an agarose gel.

3. The method of claim 2, further comprising the step:
    (i) subjecting the DNA from step (h) to a third electrophoretic migration.

4. The method of claim 3, wherein the second and third electrophoretic migrations are carried out on the same gel, the direction of migration of the DNA fragments between the second and third migration being reversed.

5. The method of claim 3, further comprising the step:
    (F) subjecting the DNA from step (i) to a fourth electrophoretic migration.

6. The method of claim 3, wherein the second and third migrations are carried out on two different gels, the direction of migration of the DNA fragments between the second and third migrations being reversed.

7. The method of claim 6, wherein the direction of the fourth migration is identical to that of the third migration.

8. The method of claim 1, wherein the DNA is recovered by electroelution or digestion of the agarose.

9. The method of claim 1, wherein the sample is an insect.

10. The method of claim 9, wherein said insect is *Drosphila* and DNA is extracted from unfertilized eggs from *Drosophila* virgin females.

11. The method of claim 1, wherein the sample is selected from the group consisting of a soil sample, a water sample, sediment sample, plant sample, human sample, non-human animal sample and insect sample.

12. The method of claim 11, wherein the sample is feces from a human or non-human animal.

* * * * *

UNITED STATES PATENT AND TRADEMARK OFFICE
CERTIFICATE OF CORRECTION

PATENT NO. : 6,989,249 B2
DATED : January 24, 2006
INVENTOR(S) : Nalin et al.

It is certified that error appears in the above-identified patent and that said Letters Patent is hereby corrected as shown below:

Column 16,
Line 40, delete "(F)" and insert -- (j) --.

Signed and Sealed this

Twenty-fifth Day of April, 2006

JON W. DUDAS
*Director of the United States Patent and Trademark Office*